(12) United States Patent
Cui et al.

(10) Patent No.: US 7,258,769 B2
(45) Date of Patent: Aug. 21, 2007

(54) ELECTROCHEMICAL BIOSENSORS

(75) Inventors: Gang Cui, Yanji (CN); Ju-Yong Kim, Suwon (KR); Moon-Hwan Kim, Gogangbon-dong (KR)

(73) Assignee: I-Sens, Inc. (KR)

( * ) Notice: Subject to any disclaimer, the term of this patent is extended or adjusted under 35 U.S.C. 154(b) by 640 days.

(21) Appl. No.: 10/416,237

(22) PCT Filed: Apr. 17, 2002

(86) PCT No.: PCT/KR02/00703
§ 371 (c)(1),
(2), (4) Date: May 7, 2003

(87) PCT Pub. No.: WO03/056345
PCT Pub. Date: Jul. 10, 2003

(65) Prior Publication Data
US 2004/0045821 A1    Mar. 11, 2004

(30) Foreign Application Priority Data
Dec. 24, 2001    (KR) ............................ 2001-84331

(51) Int. Cl.
*G01N 27/327*    (2006.01)

(52) U.S. Cl. .................... 204/403.14; 204/403.01; 204/403.1; 204/403.11

(58) Field of Classification Search .................. 204/403.01–403.15
See application file for complete search history.

(56) References Cited

U.S. PATENT DOCUMENTS 5,264,103 A  *  11/1993  Yoshioka et al. ............ 205/778
5,494,562 A  *  2/1996   Maley et al. ................ 257/414
5,562,770 A     10/1996  Chen et al.
5,798,031 A     8/1998   Charlton et al.
6,218,134 B1 *  4/2001   Yamauchi et al. ........... 435/7.9
6,270,637 B1    8/2001   Crismore et al.
6,558,528 B1 *  5/2003   Matzinger ................ 205/777.5

FOREIGN PATENT DOCUMENTS

JP    09-101280 A  *  4/1997
WO    WO97/02487       1/1997

OTHER PUBLICATIONS

English language computer translation of Tadahisa et al. (JP 09-101280 A) application published Apr. 15, 1997.*
Cui et al. ("Disposable amperometric glucose sensor electrode with enzyme-immobilized nitrocellulose strip," Talanta 54 (1002) 1105-1111).*
Chen et al. ("Bioinorganic Composites for Enzyme Electrodes," Anal. Chem. 2001, 73, 2862-2868).*

* cited by examiner

*Primary Examiner*—Alex Noguerola
(74) *Attorney, Agent, or Firm*—Bachman & LaPointe, P.C.

(57) ABSTRACT

There is provided electrochemical biosensors with a sample introducing part, comprising a sample introducing passage, an air discharge passage, and a void. The sample introducing passage communicates with the air discharge passage, and the void is formed at the point of communication. Also, disclosed is the electrochemical biosensor with the said sample introducing part and a fluidity determining electrode.

14 Claims, 10 Drawing Sheets

FIG. 3
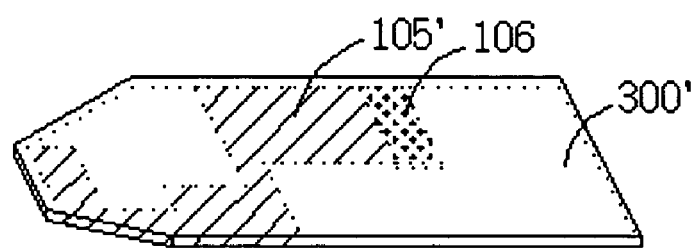
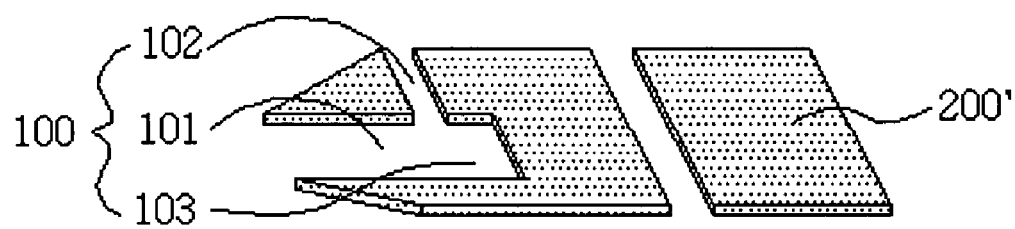
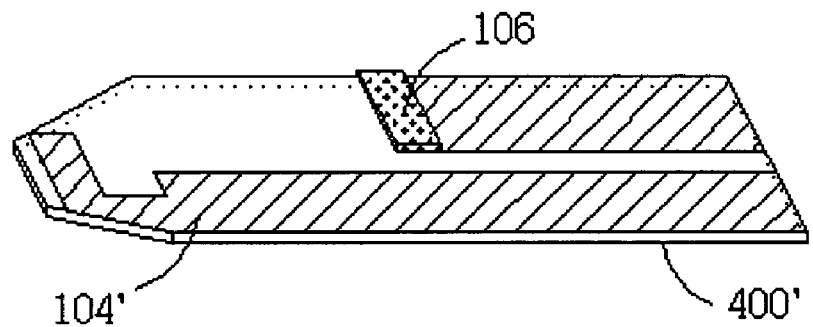

FIG. 6
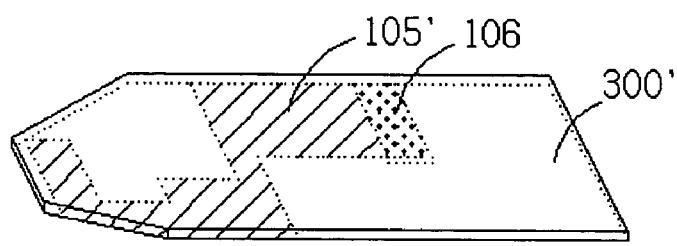
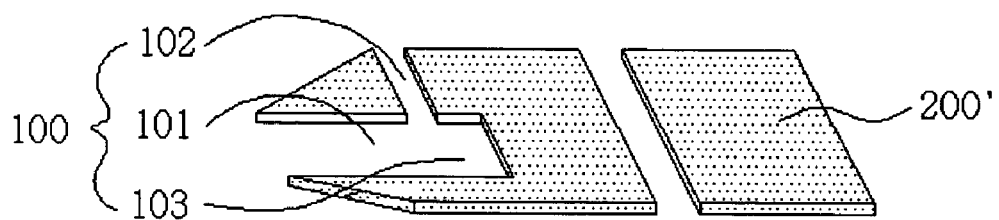
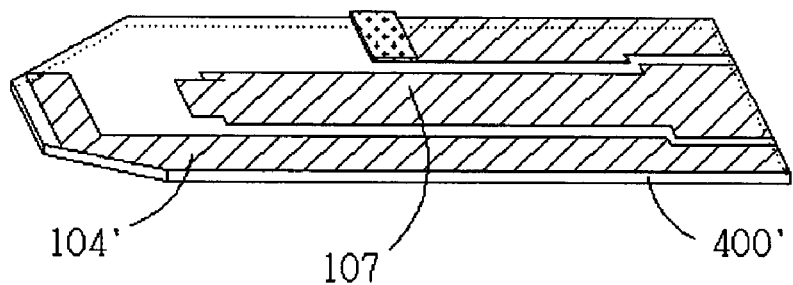

ELECTROCHEMICAL BIOSENSORS

CROSS REFERENCE TO RELATED APPLICATIONS

This patent application claims the benefit of priority from Korean Patent Application No. 10-2001-0084331 filed 24 Dec., 2001 through PCT Application Ser. No. PCT/KR02/00703 filed 17 Apr., 2002 the contents of which are incorporated herein by reference.

FIELD OF THE INVENTION

The present invention relates to electrochemical biosensors. More particularly, the present invention relates to electrochemical biosensors with an enhanced sample introducing part; the sample introducing part comprising a sample introducing passage, an air discharge passage, and a void, wherein the sample introducing passage communicates with the air discharge passage and wherein the void is formed at the point of communication. The present invention also provides a method for determining the fluidity of blood samples utilizing the said sample introducing part.

BACKGROUND OF THE INVENTION

Periodic monitoring of blood glucose levels is needed for the diagnosis and prophylaxis of diabetes mellitus. The conventional analyzers for detecting the level of glucose in blood are strip-type analyzers based on either a colorimetric method or an electrochemical method.

The colorimetric method depends on a glucose oxidase-colorimetric reaction:

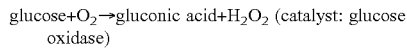

glucose+$O_2$→gluconic acid+$H_2O_2$ (catalyst: glucose oxidase)

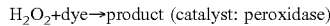

$H_2O_2$+dye→product (catalyst: peroxidase)

As shown in the reaction, glucose reacts with oxygen and is oxidized to gluconic acid and hydrogen peroxide in the presence of glucose oxidase. With the aid of peroxidase, the hydrogen peroxide is then reduced to water while oxydizing chromophoric oxygen receptor. This reaction result in color change proportional to the level of glucose in blood.

This colorimetric method, however, requires precise care, because the change of the color (or intensity) depends on the degree of sample transport and sample pre-treatment, quantity of sample, reaction time and coloration time. In addition, blood coagulation or the presence of interfering materials (for example, uric acid, ascorbic acid, and bilirubin) may disturb the colorimetric analysis.

Electrochemical method may avoid the above problems, providing high selectivity and sensitivity. For example, an electrochemical biosensor enables samples to be introduced without pre-treatment, even if the samples are turbid, and makes it possible to accurately analyze the level of glucose within a short period of time.

Both colorimetric and electrochemical methods which use oxygen as an electron transfer mediator are called as the first-generation biosensor. The second-generation electrochemical adopt organometallic compounds (e.g., Fe, Os, Ru containing derivatives), quinones, quinone derivatives, organic conducting salts or viologen as an electron transfer mediator. The second-generation electrochemical sensors are based on the reaction:

glucose+$GOx_{-FAD}$→gluconic acid+$GOx_{-FADH2}$

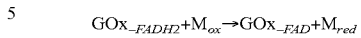

$GOx_{-FADH2}$+$M_{ox}$→$GOx_{-FAD}$+$M_{red}$ (wherein, GOx represents glucose oxidase; $GOx_{-FAD}$ and $GOx_{-FADH2}$ represent an oxidized state and a reduced state of glucose oxidase, respectively; and, $M_{ox}$ and $M_{red}$ denote the oxydized and reduced electron transfer mediator, respectively.)

As shown in the reaction, glucose is oxidized to gluconic acid by reducing $GOx_{-FAD}$ to $GOx_{-FADH2}$. The reduced glucose oxidase transfers an electron(s) to the electron transfer mediator $M_{ox}$ and then returns to the initial state. During this reaction, the redox current thus generated is measured at the surface of the electrode.

The electrochemical biosensor strip comprises: a) at least one substrate on which an electrode system (a working electrode, an auxiliary electrode and/or reference electrode) is printed, b) an oxidase and an electron transfer mediator immobilized on the electrode system, and c) a sample introducing part. The electrochemical biosensor strip may be classified into four types: (1) a flat-type biosensor in which a working electrode and an auxiliary electrode (or a reference electrode) are printed on the same base substrate; (2) a converse-type biosensor in which a working electrode and an auxiliary electrode are facing each other and; (3) a differential flat-type biosensor; and (4) a differential converse-type biosensor.

Most commercially available biosensors have a sample introducing part that might be classified as either an i-type or a horizontal line-type.

The i-type sample introducing part comprises base substrate, a thin film spacer (typically, 100-500 μm) with U-shaped cut-out portion, and the cover plate with a vent hole for discharging the air. The vent hole may be formed at the base plate as well. This type of biosensor provides a rapid introduction of liquid sample through the i-type capillary, but suffers from the disadvantages that the amount of the sample introduced is not precisely controlled because the U-shaped channel is often over filled or under filled around the vent hole; the filling of the sample channel significantly depends on the fluidity of blood which varies largely with the hematocrit level. Another disadvantage of i-type is that improper handling of the strip easily contaminates the user with the blood squeezed through the vent hole.

The horizontal line-type sample introducing part is formed by the spacer arranged to form a narrow flow channel crossing the strip between the base and cover substrates; the sample is introduced through the inlet formed on one lateral side, while an air within the space is discharged through the outlet formed on the other lateral side. This type of biosensor also suffers from the disadvantage that a sample should be introduced laterally, often forcing the user to place the strip in an awkward position over the sampling area.

Therefore, according to the first aspect of the present invention, there is provided an electrochemical biosensor equipped with a sample introducing part that enables a rapid introduction of a blood sample at the tip of the strip in accurate amount for electrochemical determination.

Human blood contains solid particles (hematocrits) such as erythrocytes, white cells and other proteins, which can be separated from the plasma; These particles change the fluidity and electrical conductivity of blood. It is noted that the sample is introduced in different speed to the capillary channel of a biosensor strip, and the sample filling time is a function of hematocrit level.

Therefore, according to the second aspect of present invention, there is provided an electrochemical biosensor equipped with a fluidity determining electrode that measures the sample fill-up time in the capillary, and a method to correct the values with respect to those at a given hematocrit level.

SUMMARY OF THE INVENTION

An object of the present invention is to provide an electrochemical biosensor with a sample introducing part that enables rapid and accurate introduction of physiological sample, without any pre-treatment of a blood sample.

Another object of the present invention is to provide an electrochemical biosensor equipped with a sample fluidity determining electrode, wherein the influences of fluidity modifying components are effectively corrected. The fluidity determining electrode also discriminates abnormal samples, such as the blood samples with unusual viscosity (too high or too low compared to that of normal human blood) or the samples containing air bubbles (U.S. Pat. No. 5,284,658).

These and other objects can be accomplished by providing the sample introducing part comprising a sample introducing passage, an air discharge passage, and a void, wherein the sample introducing passage communicates with the air discharge passage and wherein the void is formed at the point of communication, and wherein the void may be utilized further to place a fluidity determining electrode.

BRIEF DESCRIPTION OF THE DRAWINGS

The application of the preferred embodiments of the present invention is best understood with reference to the accompanying drawings, in which like reference numerals are used for like and corresponding parts, wherein:

FIG. 3 is an exploded perspective view showing a converse type biosensor, in accordance with a second embodiment of the present invention;

FIG. 6 is an exploded perspective view, which illustrates an electrochemical biosensor with a sample introducing part and a fluidity detection electrode according to the present invention;

DETAILED DESCRIPTION OF THE INVENTION

Figure 1:
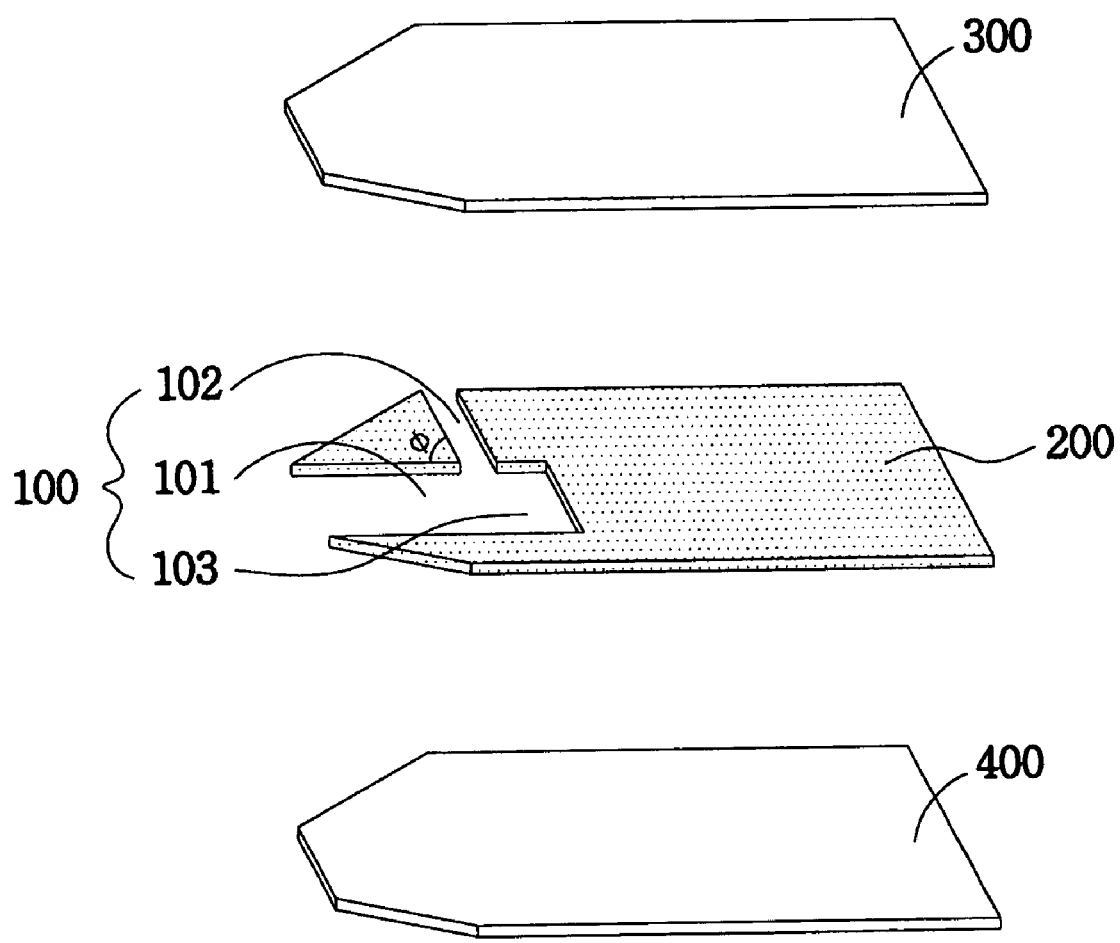
FIG. 1 is an exploded perspective view, which illustrates an electrochemical biosensor with a sample introducing part according to the present invention.

With reference to FIG. 1, an electrochemical biosensor comprises a spacer 200 and a lower substrate 400 (base) and an upper substrate (cover) 300 for forming the electrochemical sensors and sample introducing channel. Formed into one end of the spacer 200 is a sample introducing passage 101, an air discharge passage 102, and a void 103. Notably, the sample introducing passage 101 communicates with the air discharging passage 102 in a roughly perpendicular manner, and the void 103 is formed at the point of communication. Taken as a whole, the sample introducing passage 101, air discharge passage 102, and void 103 constitute a sample introducing part 100.

The sample introducing passage 101 is a passage capable of introducing the sample into the biosensor, and the air discharge passage 102 is a passage for air. Due to capillary action, a sample to be tested is introduced into the sample introducing part 100 and an air is discharged through the air discharge passage 102.

The void 103 provides for the vacant position and reduces an air-pocket phenomenon, which often occurs at the point of communication between the sample introducing passage 101 and the air discharge passage 102. The occurrence of the air-pocket phenomenon results in inaccurate measurements such that the void 103 ensures accurate and reproducible sampling.

The ratio of the width of the air discharge passage 102 to that of the sample introducing passage 101 is preferred to be no more than 1:2. The most preferable range is 1:5 to 1:2. A ratio below 1:2 ensures the containment of an exact amount of sample in channel 101 with minimal fill over through the air discharge passage 102.

In FIG. 1, the angle of communication ($\phi$) between the sample introducing passage 101 and the air discharge passage 102 is shown as 90°. But, according to another embodiment of the present invention, this angle may be varied within a range of from about 45° to about 135°, preferably, from about 75° to about 105°.

As also shown in FIG. 1., the void 103 extends beyond the point of communication from the sample introducing passage 101. To ensure an exact amount of sampling with no bubble formation, hydrophilic treatment of the sample introducing passage 101 including the void 103 is desired.

The sample introducing part 100 of the present invention has a capacity to introduce 0.1-3.0 μl of a sample. More preferably, this capacity is 0.1-1.0 μl; most preferably, the capacity is 0.3-0.7 μl. Samples less than 0.1 μl are too small to give an accurate measurement within the current biosensor's range of error. Meanwhile, samples greater than 3.0 μl are excessive. In preferred embodiments, accurate measurements have been obtained with samples of just 0.5 μl.

Pressing an organic polymer film consisting of polyester, polyvinyl chloride, or polycarbonate could make the introduction of the spacer 200 between the base and upper substrate. It could be fabricated by pressing a double-sided adhesive film made of organic polymer, or screen-printing a layer of adhesive with the pattern shown in FIG. 1.

The working principle of the sample introducing part 100 is described in detail as follows.

First, the sample is introduced to the sample introducing passage 101, by way of capillary action, as soon as the sample comes into contact with the mouth of the sample introducing passage 101, and the passage 101 is filled with the sample up to the void space 103. Extra sample is then forwarded to the air discharge passage 102. Herein, the sample fill-over can be minimized by controlling the ratio of the width of the air discharge passage 102 to that of the sample introducing passage 101 to less than 1:2, and the hydrophilic void 103 removes the air-pocket forming phenomenon occurring at the point of communication between the sample introducing passage 101 and the air discharge passage 102.

According to the preferred embodiment of the present invention, given a 0.5 µl sample capacity, the sample introducing part 100 fills with blood in about 200-2000 ms depending on the hematocrit level, sample storage conditions, and the type of anti-coagulant used. Fresh blood samples normally fills the 0.5 µl sampling channel in about 200-800 ms as a function of hematocrit level.

The sample introducing part 100 of the present invention may be applied to various types of biosensors, including a flat type biosensor, a converse type biosensor, a differential flat type biosensor, a differential converse type biosensor, or a converse biosensor with fluidity determining electrode.

Figure 2:
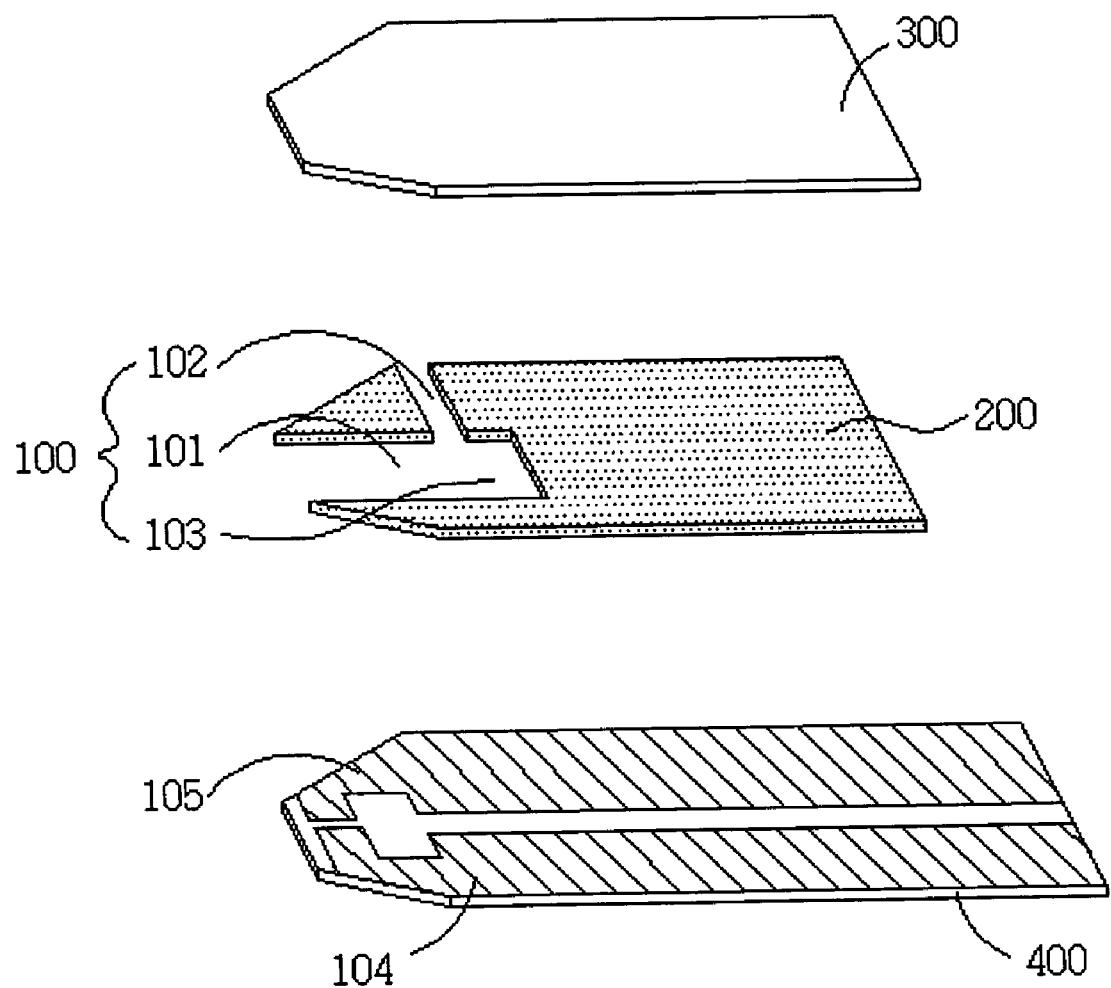
FIG. 2 is an exploded perspective view showing a flat type biosensor, in accordance with a first embodiment of the present invention.

Referring to FIG. 2, a flat type biosensor with the sample introducing part 100 of the present invention comprises a base substrate 400 on which an electrode system (a working electrode 104 and an reference electrode 105) are printed, with an oxidase and an electron transfer mediator immobilized on the electrode system; a sample introducing spacer 200 having the sample introducing part 100; and an upper substrate 300 for enclosing the sample introducing parts and for protecting the biosensor from foreign contaminants. The sample introducing part 100 may be formed as shown, but the present invention is satisfied as long as the sample introducing passage 101 communicates with the air discharge passage 102 and the void 103 is formed at the point of communication; the structure of the void 103 may also be modified as detailed above.

In the above flat type biosensor, carbon or a conductive metal material may be printed or deposited on the base substrate 400 by means of, for example, screen-printing, plasma deposition, or etching to form the working electrode 104 and the reference electrode 105. The two electrodes are formed symmetrically and extend lengthwise on the base 400. After the electrode portion is thus constructed, an oxidase and an electron transfer mediator are spread onto the electrodes.

Except electrode connecting portion, the base substrate 400 is adheres to the sample introducing spacer 200 using an adhesive. The sample introducing spacer 200 is preferably made of insulating polymer, but not limited thereto. The base substrate 400 and the upper substrate 300 are fixed using adhesives or a double-sided adhesive tape. Using similar adhesive means, the fabrication of the biosensor may be completed by pressing the upper substrate 300, serving as a cover, onto the sample introducing spacer 200.

FIG. 3 illustrates a converse type biosensor with a sample introducing part 100, characterized in that a base substrate 400' on which a working electrode 104' and an electrode connector 106 are printed, and an oxidase and an electron transfer mediator are immobilized on the working electrode 104'; a sample introducing spacer 200' having the sample introducing part 100; and an upper substrate 300' on the bottom side of which an reference electrode 105, and an electrode connector 106 are printed. The sample introducing part 100 may be formed as shown, but the present invention is satisfied as long as the sample introducing passage 101 communicates with the air discharge passage 102 and the void 103 is formed at the point of communication; the structure of the void 103 may also be modified as detailed above.

The fabrication of the converse type biosensor with the sample introducing part 100 can be accomplished in the same manner as the flat type biosensor with the sample introducing part 100.

Figure 4:
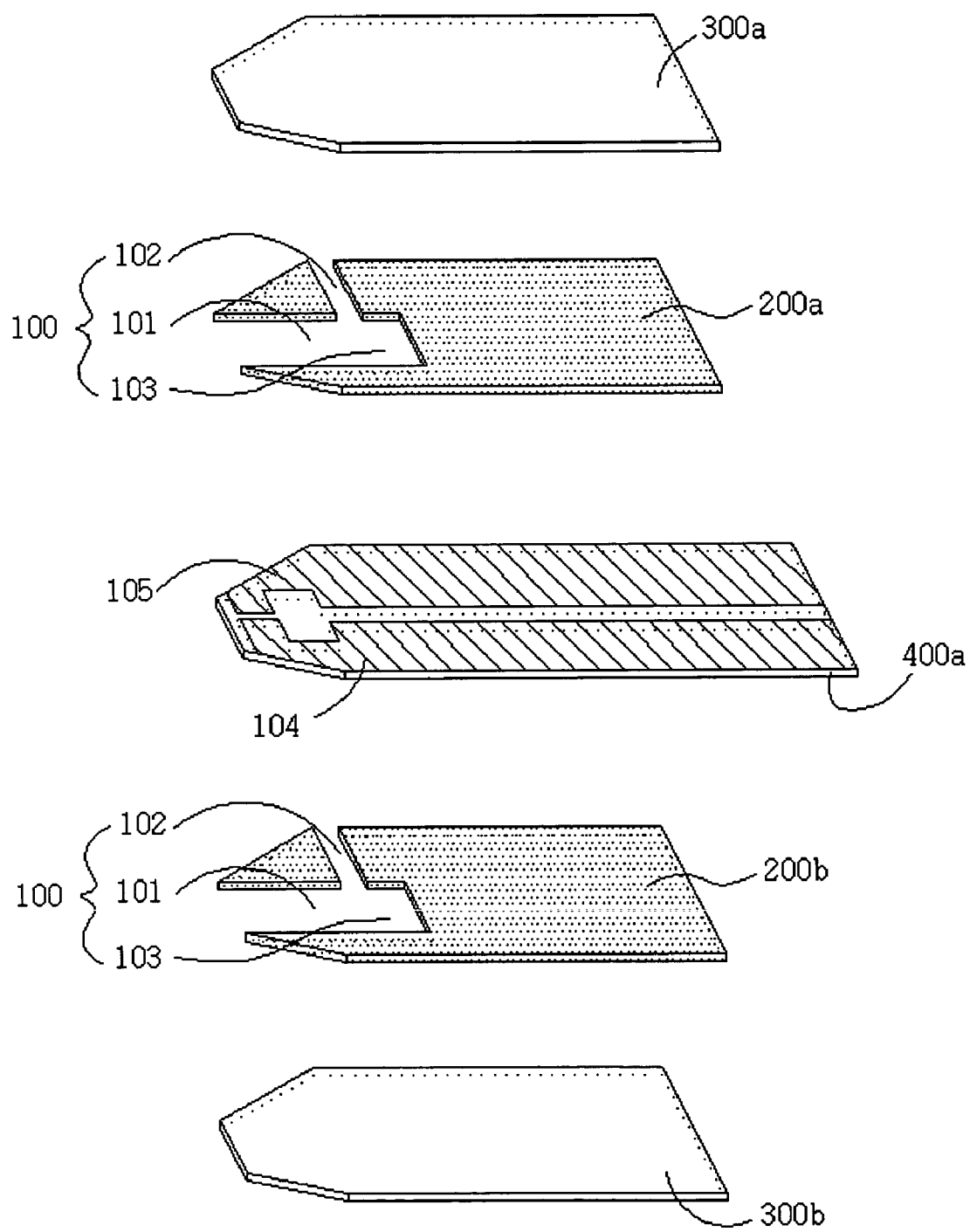
FIG. 4 is an exploded perspective view showing differential flat type biosensor, in accordance with a third embodiment of the present invention.

As shown in FIG. 4, a differential flat type biosensor comprises a base substrate 400a on both surfaces of which a working electrode 104 and an reference electrode 105 are printed and an oxidase and an electron transfer mediator are provided; a pair of sample introducing spacers 200a and 200b, each having a sample introducing part 100, respectively fixed to upper and lower surfaces of the base substrate 400a; and a pair of cover plates 300a and 300b respectively fixed to outer surfaces of the sample introducing spacers 200a and 200b. The sample introducing part 100 may be formed as shown, but the present invention is satisfied as long as the sample introducing passage 101 communicates with the air discharge passage 102 and the void 103 is formed at the point of communication; the structure of the void 103 may also be modified as detailed above.

Figure 5:
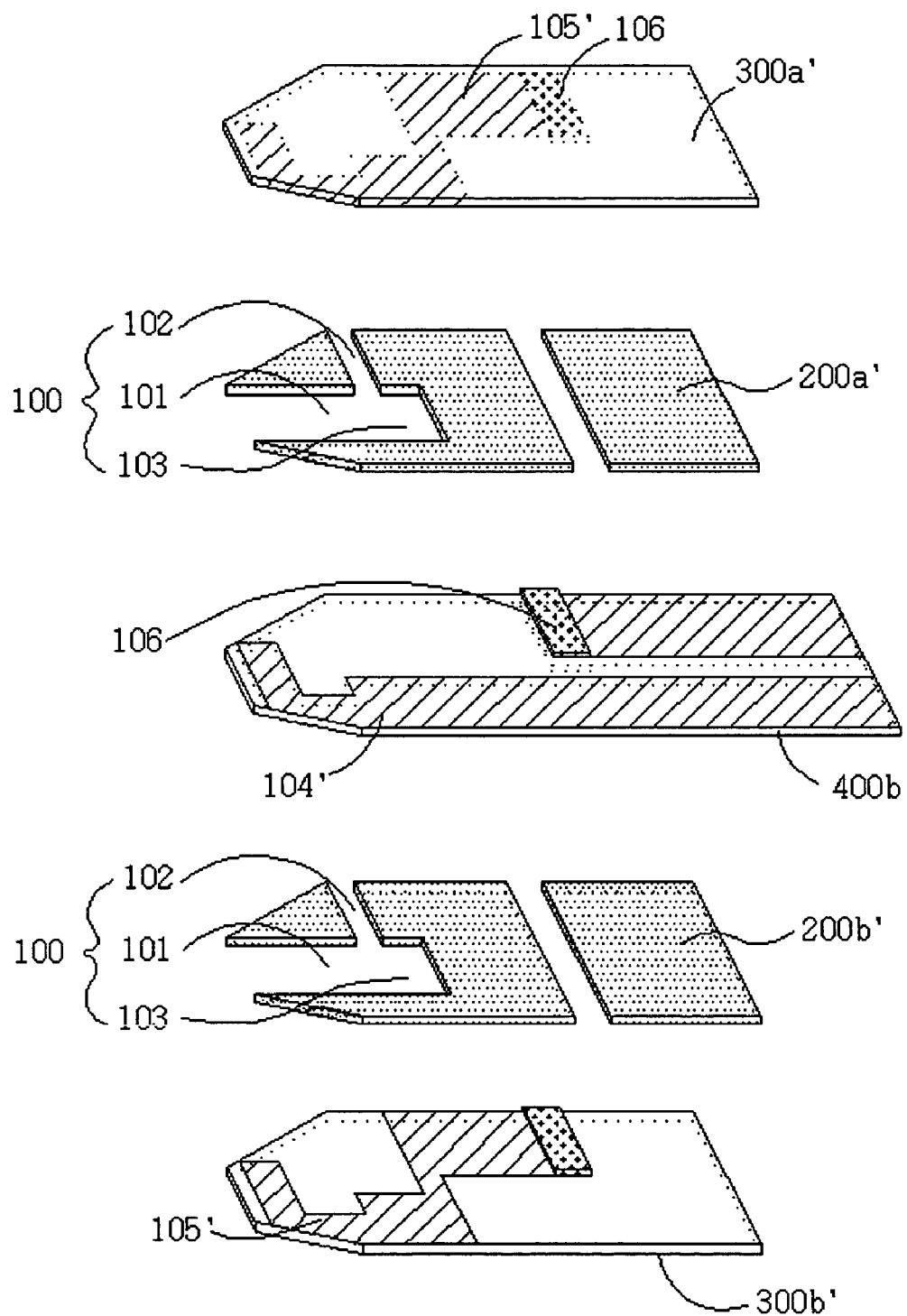
FIG. 5 is an exploded perspective view showing a differential converse type biosensor, in accordance with a fourth embodiment of the present invention.

As shown in FIG. 5, a differential converse type biosensor comprises a base substrate 400b on both surfaces of which a working electrode 104 and an electrode connector 106 are printed and an oxidase and an electron transfer mediator are provided; a pair of sample introducing spacers 200a' and 200b', each having a sample introducing substrate 100, respectively fixed to upper and lower surfaces of the base substrate 400b; and a pair of cover plates 300a' and 300b', respectively fixed to outer surfaces of the sample introducing spacers 200a' and 200b', on inner sides of which an reference electrode 105', and an electrode connector 106 are printed. The sample introducing part 100 may be formed as shown, but the present invention is satisfied as long as the sample introducing passage 101 communicates with the air discharge passage 102 and the void 103 is formed at the point of communication; the structure of the void 103 may also be modified as detailed above.

As shown in FIG. 6, illustrated is a converse type biosensor with sample fluidity determining capacity, characterized in that a base substrate 400' on which a working electrode 104', an electrode connector 106, and fluidity determining electrode 107 are printed, and an oxidase and an electron transfer mediator are immobilized on the working electrode 104'; a sample introducing spacer 200' having the sample introducing part 100; and an upper substrate 300' on the bottom side of which an reference electrode 105', and an electrode connector 106 are printed. The sample introducing part 100 may be formed as shown, but the present invention is satisfied as long as the sample introducing passage 101 communicates with the air discharge passage 102 and the void 103 is formed at the point of communication; the structure of the void 103 may also be modified as detailed above. The fluidity of a sample is determined as a function of sample filling speed between the first contact point of electrode 105' near the sample introducing mouth and the fluidity determining electrode 107 which is located either at the void 103 or at the air discharge passage 102.

The substrates of any of the base plates or cover plates for use in the biosensors described above may be made of ceramic, glass, or polymeric materials, with a preference for an organic polymer of polyester, polyvinyl chloride, or polycarbonate.

The fabrication of the electrodes, such as the reference electrodes, working electrodes, and reference electrodes, may be achieved using a conductive material, e.g., silver epoxy, silver/silver chloride, carbon, redox couples, or a modified conductive carbon paste containing a resin binder. These materials may be formed into reference, counter, and working electrodes by a screen-printing method, a vapor deposition method followed by etching, or an adhesion of a conductive tape.

The above-described biosensors with the sample introducing part 100 have several advantages.

(1) The air-pocket phenomenon, occurring at the point of communication between the sample introducing passage and air discharge passage, is eliminated while the sample is rapidly introduced into the biosensor.

(2) As the sample introducing part 100 is well enclosed by the narrow mouth and air discharge passage, the biosensors of the present invention maintain a consistent sample concentration with minimal evaporation, thus improving analytical reproducibility. In addition, the sample is better contained with the present invention than other types of sample introducing schemes when the strips are adapted to and removed from instruments, thereby considerably reducing the possibility of contamination.

(3) The biosensors equipped with the sample introducing part 100, in which the sample introducing passage and air discharge passage communicate in a roughly perpendicular manner, are capable of rapidly introducing a predetermined amount of sampled blood and increasing accuracy and reproducibility. This is in contrast to the conventional i-type biosensor.

(4) The present invention allows easier blood sampling through the tip of the biosensor when it is applied to body parts.

The electron transfer mediator provided for the working electrode may employ ferrocene or its derivatives, quinone or its derivatives, organic conducting salts, or viologen. Preferably, the electron transfer mediator is a mixed-valence compound capable of forming redox couples, including hexaamineruthenium (III) chloride, potassium ferricyanide, potassium ferrocyanide, dimethylferrocene, ferricinium, ferocene-monocarboxylic acid, 7,7,8,8-tetracyanoquinodimethane, tetrathiafulvalene, nickelocene, N-methylacridinium, tetrathiatetracene, N-methylphenazinium, hydroquinone, 3-dimethylaminobenzoic acid, 3-methyl-2-benzothiazolinone hydrazone, 2-methoxy-4-allylphenol, 4-aminoantipyrin, dimethylaniline, 4-aminoantipyrene, 4-methoxynaphthol, 3,3',5,5'-tetramethylbenzidine, 2,2-azino-di-[3-ethylbenzthiazoline sulfonate], o-dianisidine, o-toluidine, 2,4-dichloro phenol, 4-aminophenazone, benzidine, and Prussian blue. Of those, hexaamineruthenium (III) chloride is a preferred mediator for the proposed biosensor system, since it satisfies several conditions: (1) both an oxidized and a reduced states thereof in aqueous solution are stable and reversible; (2) the reduced electron transfer mediator is non-reactive to oxygen; (3) its formal potential is low enough to minimize the influence of interfering materials such as ascorbic acid, uric acid, and acetaminophen; (4) the oxidation of the reduced electron transfer mediator is not sensitive to pH; and (5) it does not react with electrochemically interfering materials, such as ascorbic acid, acetaminophen, and uric acid.

Herein, it should be understood that the present invention, although described for biosensors for analysis of blood glucose levels, can introduce appropriate enzymes and electron transfer mediators to the electrode system so that a variety of samples, including bio-materials, such as metabolites, e.g., cholesterol, lactate, creatinine, proteins, hydrogen peroxide, alcohols, amino acids, and enzymes, e.g., GPT (glutamate pyruvate transaminase) and GOT (glutamate oxaloacetate transaminase), environmental materials, agricultural and industrial materials, and food materials can be quantitatively analyzed. For instance, cholesterol, lactate, glutamate, hydrogen peroxide, and alcohol can be quantitatively analyzed using glucose oxidase, lactate oxidase, cholesterol oxidase, glutamate oxidase, horseradish peroxidase, or alcohol oxidase, respectively.

A better understanding of the present invention may be obtained in light of the following examples which are set forth to illustrate, but are not to be construed to limit the present invention.

EXAMPLE 1

Fabrication of a Flat Type Biosensor

Conductive carbon paste was screen-printed to form a symmetrical pattern on a polyester base plate 400 to give working electrode 104 and a reference electrode (or reference electrode) 105. The interval between the two electrodes is 125 μm. A curing of the printed electrodes at 140° C. for five minutes yielded a single electrode body for a flat type biosensor.

Thereafter, the sample introducing part 100, comprising the sample introducing passage 101, air discharge passage 102, and void 103 formed therein, was fixed by pressing double-sided tape made of polyester. The sample introducing passage 101 communicates perpendicularly with the air discharge passage 102, and the ratio of the width of the air discharge passage 102 to that of the sample introducing passage 101 was controlled to be 1:2. The void 103 was formed to extend beyond the sample introducing passage 101. The total amount of sampled blood within the sample introducing part 100 was 0.5 μl.

The frame for the biosensor was prepared by inserting to each polyester base plate 400 and by pressing double-sided tape made of polyester as a sample introducing spacer 200 having the sample introducing part 100. A solution containing 0.015 mg of hexaamineruthenium (III) chloride, 0.015 mg of a dispersant (carboxymethylcellulose), 0.01 mg of a surfactant (Triton X-100), and 40 mg of glucose oxidase was applied to the electrodes for forming the biosensor, and the resultant deposit was allowed to dry for thirty minutes at 45° C.

Pressing a cover plate 300 onto the sample introducing spacer 200 completed the flat type biosensor of FIG. 2.

EXAMPLE 2

Fabrication of a Converse Type Biosensor

As shown in FIG. 3, a working electrode 104' and an electrode connector 106 were screen-printed with conductive carbon paste, and a curing was carried out at 140° C. for five minutes. Then, a circuit connector was screen-printed with the silver paste on one end of the electrode connector 106. The cover plate with the printed electrode as a reference (auxiliary) electrode 105' was screen-printed with carbon paste and was cured. Finally, the biosensor was fabricated such that the end of the reference electrode 105' was screen-printed with silver paste to be the circuit connector.

The sample introducing spacer 200' comprising the sample introducing passage 101, air discharge passage 102, and void 103 was placed on the base substrate by pressing double-sided tape made of polyester. The ratio of the width of the air discharge passage 102 to that of the sample introducing passage 101 was 1:4, and the total amount of sampled blood within the sample introducing part 100 was adjusted to 0.5 μl.

A 1 ml solution containing 0.015 mg of hexaamineruthenium (III) chloride, 0.015 mg of a dispersant (carboxymethylcellulose), 0.01 mg of a surfactant (Triton X-100), and 40 mg of glucose oxidase was applied to the electrodes forming the biosensor, and the reaction layer was allowed to dry for thirty minutes at 45° C.

Pressing the cover plate 300' onto the sample introducing spacer 200', so as to connect with the circuit connector of the base substrate 400', completed the biosensor shown in FIG. 3.

EXAMPLE 3

Fabrication of a Differential Flat Type Glucose Sensor

The differential flat type glucose sensor was prepared in the same manner as in Example 1. As shown in FIG. 4, the differential flat type biosensor was fabricated by providing a small amount of bovine serum albumin (BSA) on the differential working electrode 104 of the base substrate 400a, instead of the hexaamineruthenium (III) chloride and glucose oxidase used in Example 1, and by pressing the cover plates 300a and 300b.

EXAMPLE 4

Fabrication of a Differential Converse Type Biosensor

The differential converse type glucose sensor was prepared in the same manner as in Example 2. As shown in FIG. 5, the differential converse type biosensor was fabricated by providing a small amount of bovine serum albumin (BSA) on the differential working electrode 104' of the base substrate 400b, instead of hexaamineruthenium (III) chloride and glucose oxidase used in Example 1, and by pressing the cover plates 300a' and 300b'.

EXAMPLE 5

Fabrication of Biosensor with Fluidity Determining Electrode

The biosensor with fluidity determining electrode was the converse type biosensor prepared in the same manner as in Example 2 except the use of fluidity determining electrode 107; as illustrated in FIG. 6, it was screen-printed with the same carbon paste. The tip of the fluidity-determining electrode was placed at the void 103 of the sample introducing part.

EXPERIMENTAL EXAMPLE 1

Influence of Interfering Materials on a Converse Type Glucose Sensor

Figure 7:
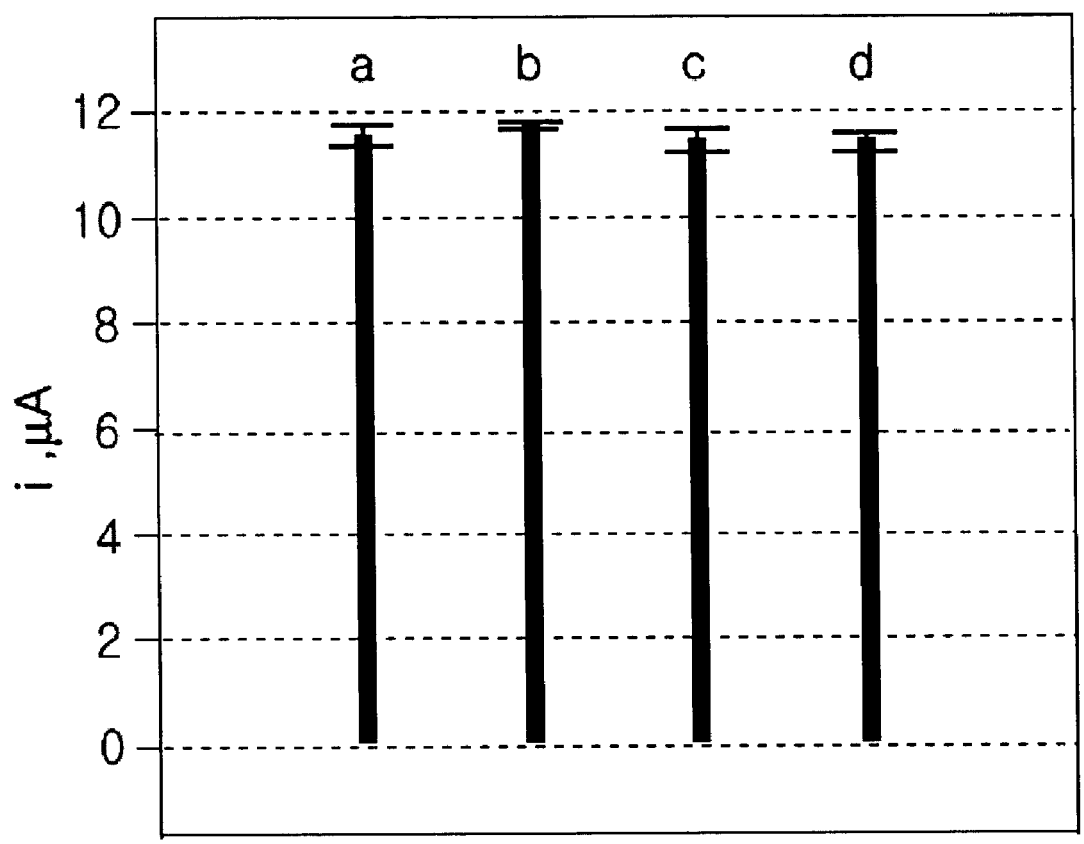
FIG. 7 is the graph that shows the influence of various interfering materials on a converse type glucose sensor;
  a: Glucose
  b: Glucose+Acetoaminophen (660 μM)
  c: Glucose+Ascorbic acid (570 μM)
  d: Glucose+Uric acid (916 μM)

FIG. 7 shows the total response currents to phosphate buffer (pH 7.4) standard solutions containing 177 mg/dL of glucose and interfering materials whose concentrations are five times higher than the maximum clinical levels (e.g., ascorbic acid 570 μM, acetaminophen 660 μM, and uric acid 916 μM). The total response currents were measured by reading the chronoamperometric response 5 seconds after applying the +0.2 V potential to the working electrode 104' (vs. reference electrode 105'). Samples were introduced into the sample introducing part 100 of the biosensor fabricated as depicted in Example 2, and their mean volume was 0.5 μL. Histograms in FIG. 7 show that the sensors are affected insignificantly by the presence of interfering materials at an applied potential of +0.2 V.

EXPERIMENTAL EXAMPLE 2

Figure 8:
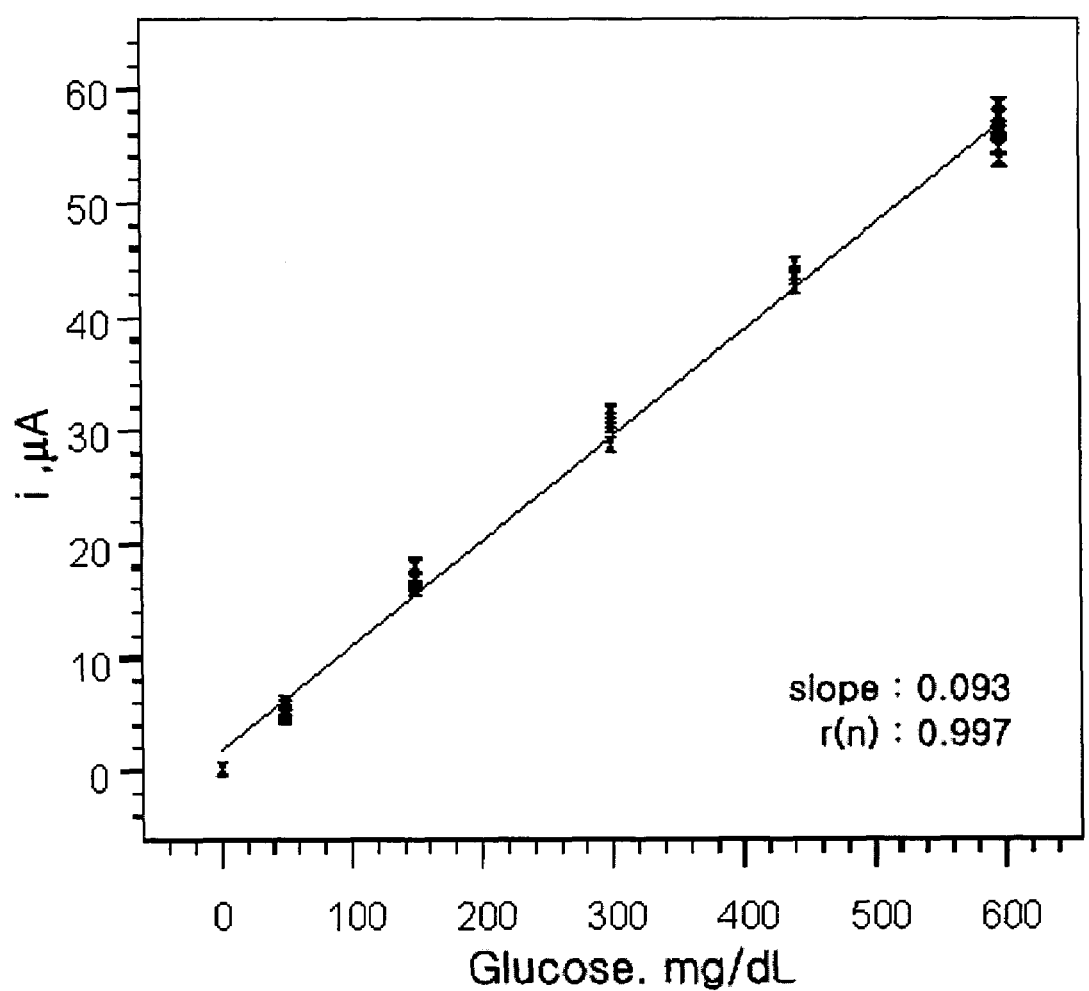
FIG. 8 is a graph showing a calibration curve of a converse type glucose sensor, for sensitivity to glucose standard solution.
Figure 9:
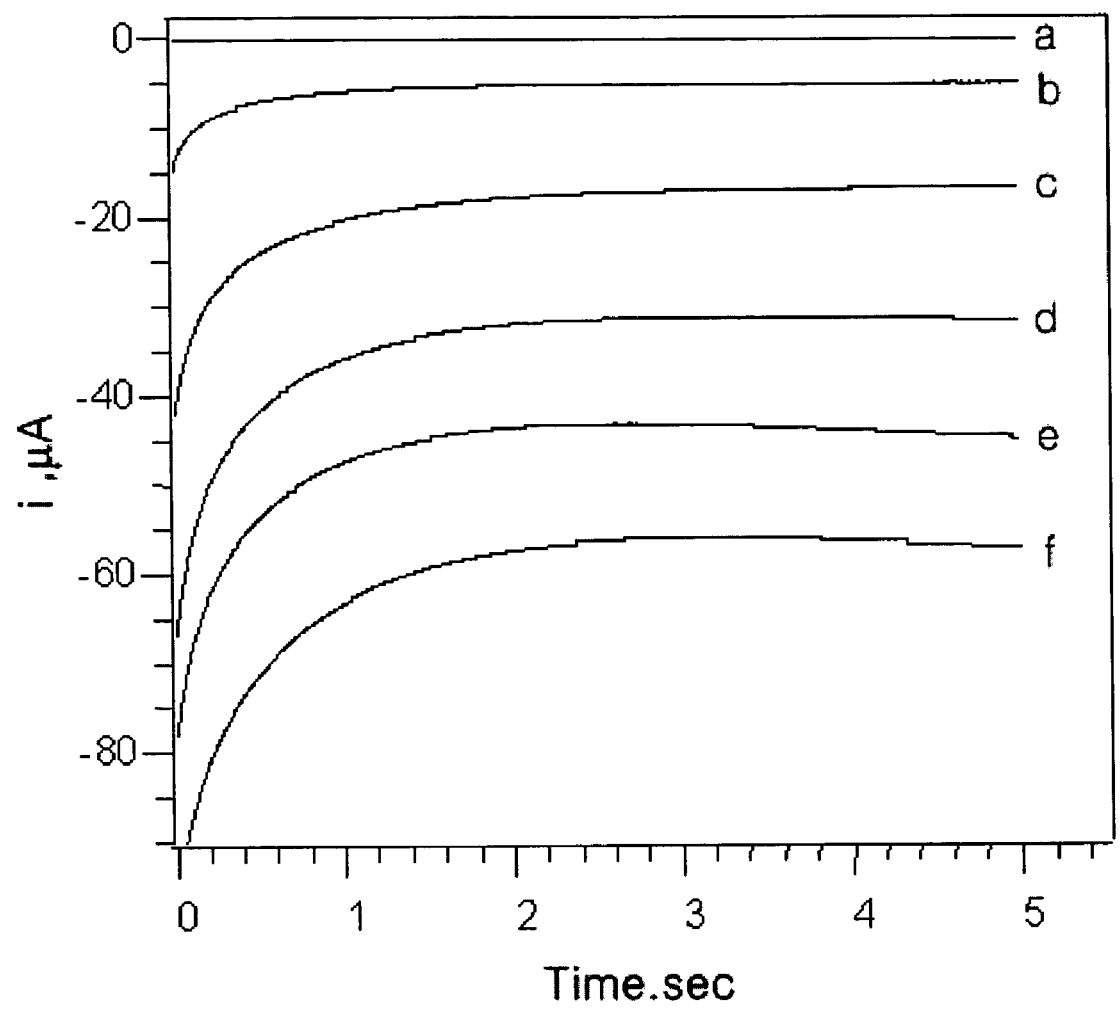
FIG. 9 is a graph showing dynamic curves, obtained by a chronoamperometric method, of a converse type glucose sensor, for glucose standard solutions.

Calibration Curve of a Converse Type Glucose Sensor to Glucose Standard Solutions The converse type glucose sensor prepared in Example 2 was assayed for sensitivity with glucose standard solutions. The calibration curve thus obtained is depicted in FIG. 8. In this regard, current values were measured ten times at each concentration under the electrical field of an applied potential of 0.2 V with respect to the reference electrode. The amount of samples applied to the sample introducing part was 0.5 μl and the filling time was no more than 200 ms. The measurements were performed 2 s after introducing the sample by applying 0.2 V for three seconds, and the current values were read in five seconds. The dynamic curves thus obtained are depicted in FIG. 9, wherein the respective curves show glucose concentrations of 0 mg/dL (curve a), 50 mg/dL (curve b), 150 mg/dL (curve c), 300 mg/dL (curve d), 450 mg/dL (curve e), and 600 mg/dL (curve f).

Demonstrating that the converse type glucose sensor of the present invention is reliable, the curve was evaluated and shown to have a slope (μA per mg/dL) of 0.093 and linearity as high as 0.997.

EXPERIMENTAL EXAMPLE 3

Measurement of the Blood Fluidity

Figure 10:
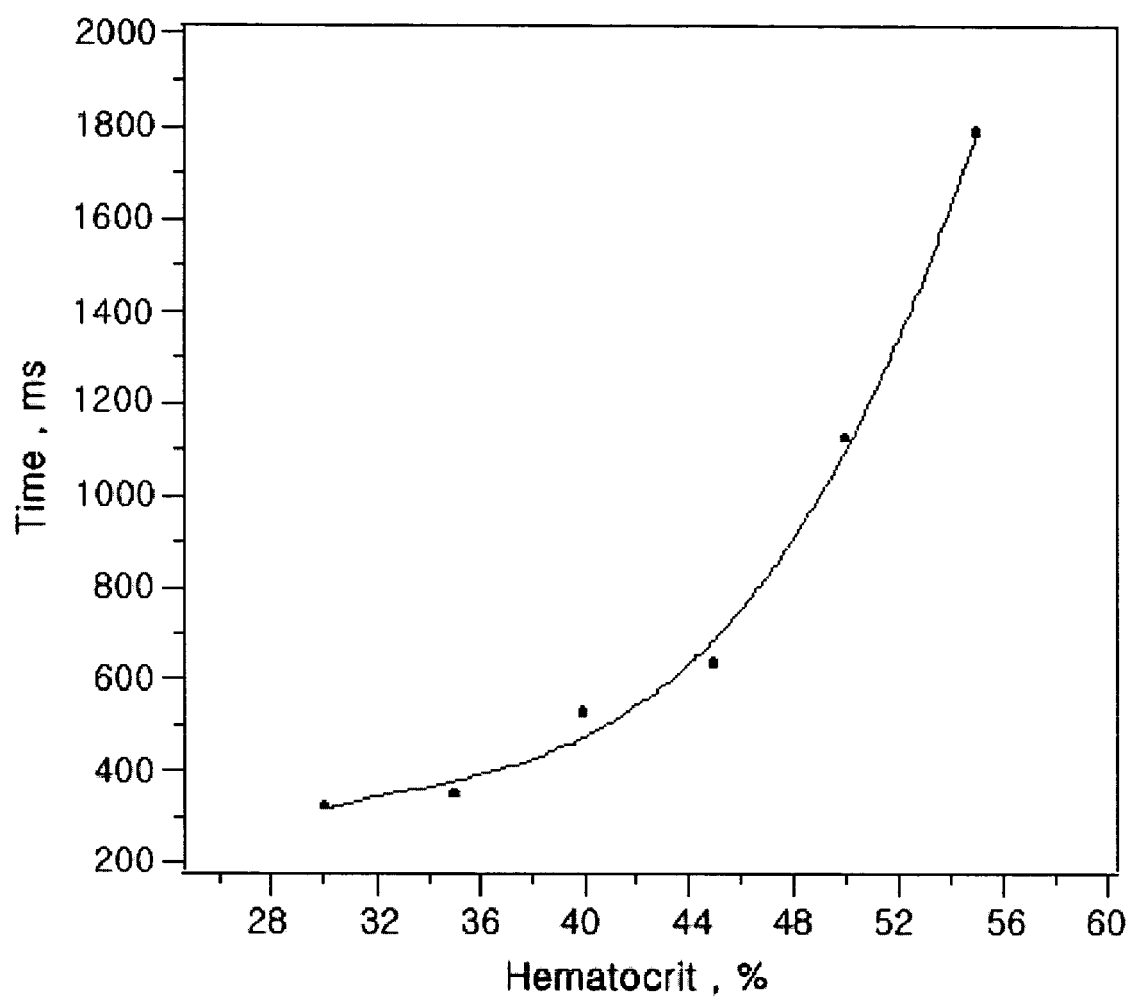
FIG. 10 is a graph that illustrates the relationship between the sample fluidity (as a function of time) and the hematocrit level.

The biosensor equipped with fluidity determining electrode was prepared as described in Example 5. 200 mV of potential was applied to the working electrode 104' and the fluidity determining electrode 107 (vs. the reference electrode 105'). When blood samples are introduced through the sample introducing passage 101, a sudden change in current is detected, and the time measurement begins. As soon as the sample reaches the void 103, the second surge of current is detected and the time interval between the first and second surge of current is recorded. The relationship between the sample introducing time and hematocrit level is shown in FIG. 10. The experiment was performed with the NaF treated whole blood containing 180 mg/dL of glucose and varying level of hematocrit. The fitting equation obtained was $Y=-72.23+0.58691X-0.00084073X^2-1.1211\times10^{-6}X^3+5.752\times10^{-9}X^4-9.1172\times10^{-12}X^5$, where Y is the estimated hematocrit level from the sample filling time X measured with the fluidity determining electrode. Table 1 shows the level of hematocrit estimated from the speed of sample filling time.

TABLE 1

Hematocrit level estimated from the sample filling time of the biosensor prepared in Example 5.

| Hematocrit (%) Prepared sample | Speed (ms) | Estimated Hematocrit (%) |
|---|---|---|
| 30% | 326 | 30.3% |
| 35% | 352 | 32.8% |

TABLE 1-continued

Hematocrit level estimated from the sample filling time of the biosensor prepared in Example 5.

| Hematocrit (%) Prepared sample | Speed (ms) | Estimated Hematocrit (%) |
|---|---|---|
| 40% | 530 | 41.8% |
| 45% | 634 | 44.0% |
| 50% | 1129 | 50.1% |
| 55% | 1791 | 54.7% |

In a separate experiment, calibration curves were obtained with the whole blood at various hematocrit levels and the relationship between the hematocrit level and the response slopes was formulated (Table 2).

| Hematocrit | Equation (y = current µA; x = glucose) |
|---|---|
| 30% | y = 0.035934 x − 1.7228 |
| 35% | y = 0.030559 x − 1.31815 |
| 40% | y = 0.025831 x − 1.0137 |
| 45% | y = 0.021752 x − 0.80945 |
| 50% | y = 0.018322 x − 0.7054 |
| 55% | y = 0.015539 x − 0.70155 |

The correction factors derived in this manner were used to recalibrate the measured glucose level with respect to the whole blood having 40% hematocrit level, resulting in the biosensors that provide hematocrit independent glucose concentrations. The meter reads the speed of sample introduction first and determines the level of hematocrit in the blood sample, looks up the table that provides the corresponding calibration curves, and determines the level of glucose from the measured currents. Table 3 shows the results of the experiment carried out as outlined. It is seen that the hematocrit level correction provides the glucose levels close to those obtained with YSI 2300. Table 3. Glucose concentration in whole blood; the sample introducing speed measured with the fluidity determining electrode and the calibration curve in Table 2 were used to estimate the glucose level in whole blood.

| Hematocrit % | Glucose YSI2300 (mg/dL) | Hematocrit corrected (mg/dL) |
|---|---|---|
| 30% | 111 | 117 |
|  | 202 | 186 |
|  | 381 | 392 |
| 35% | 138 | 141 |
|  | 200 | 207 |
|  | 276 | 277 |
| 40% | 107 | 112 |
|  | 196 | 195 |
|  | 266 | 264 |
| 45% | 103 | 105 |
|  | 190 | 189 |
|  | 367 | 363 |
| 50% | 102 | 107 |
|  | 142 | 143 |
|  | 253 | 256 |
| 55% | 125 | 144 |
|  | 241 | 240 |
|  | 332 | 331 |

The fluidity determining electrode also discriminate the blood samples of unusual fluidity, i.e., samples with too high or too low hematocrit levels and the fouled introduction of blood samples due to the formation of air bubble. In such cases a measuring device may be programmed to issue a warning message or error code for the measurement.

What is claimed is:

1. An electrochemical biosensor with a sample introducing part, the sample introducing part comprising a sample introducing passage, an air discharge passage, and a void, wherein the sample introducing passage communicates with the air discharge passage in a substantially perpendicular manner, wherein the void is formed at the point of communication from the sample introducing passage and wherein the ratio of the width of the air discharge passage to that of the sample introducing passage is no more than 1:2.

2. The electrochemical biosensor according to claim 1, wherein the ratio of the width of the air discharge passage to that of the sample introducing passage is in the range of 1:5 to 1:2.

3. The electrochemical biosensor according to claim 1, wherein the sample introducing part has a capacity to introduce 0.1-3.0 µl of a sample.

4. The electrochemical biosensor according to claim 1, wherein the sample introducing part has a capacity to introduce 0.11.0 µl of a sample.

5. The electrochemical biosensor according to claim 1, wherein the sample introducing part has a capacity to introduce 0.3-0.7 µl of a sample.

6. The electrochemical biosensor according to claim 1, wherein the sample introducing passage communicates with the air discharge passage at an angle of 90°.

7. The electrochemical biosensor according to claim 1, further comprising an oxidase selected from the group consisting of glucose oxidase, lactate oxidase, cholesterol oxidase, glutamate oxidase, horseradish peroxidase, and alcohol oxidase.

8. The electrochemical biosensor according to claim 1, further comprising an electron transfer mediator selected from the group consisting of hexaamineruthenium (III) chloride, potassium ferricyanide, potassium ferrocyanide, dimethylferrocene, ferricinium, ferocene-monocarboxylic acid, 7,7,8,8-tetracyanoquinodimethane, tetrathiafulvalene, nickelocene, N-methylacidinium, tetrathiatetracene, N-methylphenazinium, hydroquinone, 3-dimethylaminobenzoic acid, 3-methyl-2-benzothiozolinone hydrazone, 2-methoxy-4-allylphenol, 4-aminoantipyrin, dimethylaniline, 4-aminoantipyrene, 4-methoxynaphthol, 3,3',5,5'-tetramethylbenzidine, 2,2-azino-di-[3-ethylbenzthiazoline sulfonate], o-dianisidine, o-toluidine, 2,4-dichloro phenol, 4-aminophenazone, benzidine and Prussian blue.

9. The electrochemical biosensor according to claim 8, wherein the electron transfer mediator is hexaamineruthenium (III) chloride.

10. The electrochemical biosensor according to claim 1, wherein the biosensor is a flat type biosensor and further comprises:
    a sample introducing spacer;
    a base substrate, coupled to said sample introducing spacer, on a surface of which a working electrode and a reference electrode are printed and an oxidase and an electron transfer mediator are provided; and
    a cover plate, pressed to said sample introducing spacer, for forming the sample introducing channel,
    wherein the sample introducing part is formed in one end of said sample introducing spacer.

11. The electrochemical biosensor according to claim 1, wherein the biosensor is a converse type biosensor and further comprises:

a sample introducing spacer;

a base plate, coupled with said sample introducing spacer, on a surface of which a working electrode and an electrode connector are printed and an oxidase and an electron transfer mediator are provided; and a cover plate, pressed to said sample introducing spacer, on inner surface of which a reference electrode and an electrode connector are printed, wherein the sample introducing part is formed in one end of said sample introducing spacer.

12. The electrochemical biosensor according to claim 1, wherein the biosensor is a differential flat type biosensor and further comprises:

a pair of sample introducing spacers;

a base plate, coupled between said sample introducing spacers, on both surfaces of which a pair of working and reference electrodes are printed, respectively, and an oxidase and an electron transfer mediator on one side, and BSA and an electron transfer mediator on the other side are provided, respectively; and a pair of cover plates are pressed to both surfaces of said sample introducing spacers for forming the sample introducing channels, wherein the sample introducing parts are formed in one end of each of said sample introducing spacers.

13. The electrochemical biosensor according to claim 1, wherein the biosensor is a differential converse type biosensor and further comprises:

a pair of sample introducing spacers;

a base plate, coupled between said sample introducing spacers, on both surfaces of which a working electrode is printed, respectively, and an oxidase and an electron transfer mediator on one side, and BSA and an electron transfer mediator on the other side are provided, respectively; and a pair of cover plates having reference electrode and electrode connection part on inner surface are pressed to both said sample introducing spacers to form the sample introducing channels, wherein the sample introducing parts are formed in one end of each of said sample introducing spacers.

14. The electrochemical biosensor according to claim 1, wherein the biosensor is a converse type biosensor and further comprises:

a sample introducing spacer;

a base plate, coupled with said sample introducing spacer, on a surface of which a working electrode and an electrode connector, and a fluidity determining electrode are printed, and an oxidase and an electron transfer mediator are provided; and a cover plate, pressed to said sample introducing spacer, on inner surface of which a reference electrode and an electrode connector are printed, wherein the sample introducing part is formed in one end of said sample introducing spacer.

* * * * *

UNITED STATES PATENT AND TRADEMARK OFFICE
CERTIFICATE OF CORRECTION

PATENT NO. : 7,258,769 B2  Page 1 of 1
APPLICATION NO. : 10/416237
DATED : August 21, 2007
INVENTOR(S) : Gang Cui et al.

It is certified that error appears in the above-identified patent and that said Letters Patent is hereby corrected as shown below:

In column 12, claim 4, line 23 "0.11.0" should read --0.1-1.0--.

Signed and Sealed this

Sixth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,258,769 B2  
APPLICATION NO. : 10/416237  
DATED : August 21, 2007  
INVENTOR(S) : Gang Cui et al.

Page 1 of 1

It is certified that error appears in the above-identified patent and that said Letters Patent is hereby corrected as shown below:

On the Title Page, item [75]: Inventors should read as follows:

--Inventors: Gang Cui, Yanji (CN); Ju-Yong Kim, Suwon (KR); Moon-Hwan Kim, Gogangbon-dong (KR); Jung-Hee Uhm, Seoul (KR); Hakhyun Nam, Seoul (KR); Geun-Sig Cha, Seoul (KR)--

Signed and Sealed this  
Eighteenth Day of October, 2011

David J. Kappos  
*Director of the United States Patent and Trademark Office*